United States Patent
Rubner et al.

(10) Patent No.: US 11,849,998 B2
(45) Date of Patent: *Dec. 26, 2023

(54) METHOD FOR PUPIL DETECTION FOR COGNITIVE MONITORING, ANALYSIS, AND BIOFEEDBACK-BASED TREATMENT AND TRAINING

(71) Applicant: BIOEYE LTD., Hofit (IL)

(72) Inventors: Yossi Rubner, Shoham (IL); Eran Ferri, Hofit (IL)

(73) Assignee: BIOEYE LTD., Hofit (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/812,754

(22) Filed: Jul. 15, 2022

(65) Prior Publication Data

US 2022/0361746 A1    Nov. 17, 2022

Related U.S. Application Data

(63) Continuation of application No. 16/482,589, filed as application No. PCT/IL2017/051382 on Dec. 25, 2017, now Pat. No. 11,389,058.

(30) Foreign Application Priority Data

Feb. 5, 2017    (IL) .......................................... 250438

(51) Int. Cl.
*A61B 3/11*    (2006.01)
*A61B 5/16*    (2006.01)
(Continued)

(52) U.S. Cl.
CPC ................ *A61B 3/11* (2013.01); *A61B 5/163* (2017.08); *A61B 5/375* (2021.01); *A61B 3/113* (2013.01);
(Continued)

(58) Field of Classification Search
CPC .......... A61B 3/11; A61B 5/163; A61B 5/375; A61B 3/113; A61B 5/1103; A61B 5/1114;
(Continued)

(56) References Cited

U.S. PATENT DOCUMENTS 6,422,870 B1 * 7/2002 Ohsawa ................. A61B 3/113
434/236
7,438,418 B2    10/2008 Marshall
(Continued)

FOREIGN PATENT DOCUMENTS

WO    2015027079 A1    2/2015
WO    2018134814 A1    7/2018

OTHER PUBLICATIONS

Deng, J. Y. et al., "Region-based template deformation and masking for eye-feature extraction and description." Pattern Recognition 30.3 (1997): pp. 403-419.
(Continued)

*Primary Examiner* — Mohammed A Hasan
(74) *Attorney, Agent, or Firm* — Mendelsohn Dunleavy, P.C.

(57) ABSTRACT

The present invention relates to a system and method for pupil tracking and eye-markers extracting using an image acquisition device such as a visible-light camera shooting a non-static head. In an embodiment of the present invention eye-markers are extracted from one eye or from both eyes. The extraction from both eyes uses for averaging the results of the two eyes when abnormalities are detected in one of the eyes. In addition, the invention relates to a computerized application, which interacts with a user (for example trough a game or movie, usually in a context of biofeedback), and takes video shooting of the users face and eyes during said interaction.

14 Claims, 8 Drawing Sheets

(51) Int. Cl.
    *A61B 5/375* (2021.01)
    *A61B 3/113* (2006.01)
    *A61B 5/11* (2006.01)
    *G06F 3/01* (2006.01)

(52) U.S. Cl.
    CPC ............ *A61B 5/1103* (2013.01); *A61B 5/1114* (2013.01); *G06F 3/013* (2013.01)

(58) Field of Classification Search
    CPC ..... A61B 5/16; G06F 3/013; G06F 2203/011; G06F 3/0481
    USPC ........................................................ 351/205
    See application file for complete search history.

(56) References Cited

U.S. PATENT DOCUMENTS

| | | | |
|---|---|---|---|
| 7,444,017 B2 | 10/2008 | Gallagher | |
| 9,370,302 B2* | 6/2016 | Krueger | .................. A61B 3/113 |
| 11,389,058 B2* | 7/2022 | Rubner | .................... A61B 5/16 |
| 2006/0165266 A1 | 7/2006 | Hamza | |
| 2014/0114889 A1 | 4/2014 | Dagum | |
| 2014/0178849 A1 | 6/2014 | Yang | |
| 2015/0116665 A1* | 4/2015 | Finkel | .................... G16H 30/40 |
| | | | 351/210 |
| 2016/0117544 A1 | 4/2016 | Hoyos et al. | |
| 2016/0302713 A1 | 10/2016 | Maruta et al. | |
| 2017/0251985 A1 | 9/2017 | Howard | |
| 2018/0008141 A1* | 1/2018 | Krueger | ............... A61B 3/0025 |
| 2018/0125356 A1 | 5/2018 | Yamada | |
| 2018/0125404 A1 | 5/2018 | Bott et al. | |
| 2018/0125405 A1 | 5/2018 | Yamada | |
| 2018/0125406 A1 | 5/2018 | Yamada | |
| 2018/0239144 A1 | 8/2018 | Woods et al. | |
| 2018/0333092 A1 | 11/2018 | Roshan et al. | |

OTHER PUBLICATIONS

Canny J. F. "A computation approach to edge detection." IEEE Trans. Pattern Anal. Mach. Intell. 8.6 (1986): pp. 670-700.
Ballard, Dana H. "Generalizing the Hough transform to detect arbitrary shapes." Pattern recognition 13.2 (1981): pp. 111-122.
Mulligan, Jeffrey B. "Image processing for improved eye-tracking accuracy." Behavior Research Methods, Instruments, & Computers 29.1 (1997): pp. 54-65.
Applicant Response to the International Preliminary Report on Patentability for International Patent Application No. PCT/IL2017/051382; dated Oct. 18, 2018.
International Search Report and Written Opinion for International Patent Application No. PCT/IL2017/051382; dated Apr. 29, 2018.

* cited by examiner

METHOD FOR PUPIL DETECTION FOR COGNITIVE MONITORING, ANALYSIS, AND BIOFEEDBACK-BASED TREATMENT AND TRAINING

CROSS-REFERENCE TO RELATED APPLICATIONS

This application is a continuation of U.S. patent application Ser. No. 16/482,589, filed on Jul. 31, 2019, the teachings of which application are incorporated herein by reference in their entirety.

FIELD OF THE INVENTION

The invention relates to the field of human cognitive monitoring through eye measures analysis using computer vision and image processing. More specifically, the present invention relates to a method for pupil detection using a standard digital image acquisition device for cognitive monitoring, analysis and biofeedback sensor based treatment and training.

BACKGROUND OF THE INVENTION

Cognitive performance can be monitored and trained using physiological measures. Like other competencies, cognitive capabilities stem from a combination of "nature vs nurture" parameters, namely those inherited via genetics and those related to learning and development via exposure to the environment. Cognitive improvement solutions using biofeedback are common in many fields, starting with the treatment of people with disorders like ADHD, PDD and head injuries, to people who seek to improve their cognitive abilities (e.g., athletes, students or managers).

Biofeedback is a closed-loop process of using a biosensor (measuring one or more biometric markers) to modify (normally improve) user performance/condition/behavior by providing the user with feedback promoting a desired change.

Combining the high efficiency and transferability of biofeedback solutions with the ubiquity of computer and mobile applications, may supply a good solution for cognitive enhancement.

Recent research indicates that changes in physiological and psychological state are reflected in eye measures (such as, but not limited to pupil diameter, saccades and blinks). However, standard means of analyzing eye measures require the use of very expensive equipment, such as special IR cameras which are not commonly accessible. Operation of such equipment typically requires professional knowhow, thus making it out of reach for daily usage by the general public.

Therefore, a solution is needed, which uses a standard digital image acquisition device for this exact purpose. To the best of the inventors knowledge such attempt to monitor the eyes and pupil by use of regular equipment (e.g., a video camera in a standard smartphone) has not yet been accomplished. A main challenge when attempting to analyze eyes data for such cognition related purposes is the need for highly accurate extraction of markers (such as pupil diameter, pupil center location, blinks and their changes over time) from a video stream or file.

Other challenges that need to be addressed when extracting pupil and eye metrics using standard digital image acquisition device (such as in a smartphone front cameras) are: adjusting to limited quality camera, dynamic lighting conditions (brightness, backlight, reflections), dark eyes (lack of contrast for some users), dynamic background, dynamic face distance, instability of hand (i.e. camera movement), partial eye coverage (by eyelids), angle (non-front) capturing, latency, personalized calibration/re-calibration, glasses, contacts-lenses and of course the need to provide results based on real time processing.

Basically, three main challenges have to be resolved in order to detect the pupil and extract accurate eye measures in real time. Firstly, identifying the eyes, secondly tracking the iris and thirdly tracking the pupil.

The eye tracking problem deals with detection and localization of an eye (or both eyes) of an observed human. In existing solutions, the exact location and the size of the eye typically remain undetermined and a bounding box, ellipse, or circle are used to make it. There are existing widely-used open-source implementations of eye tracking (for example—http://opencv.org/), however these existing solutions returns many false-positive results of the eye locations, therefore degrading the accuracy of the results.

The iris tracking problem deals with the exact localization of the iris, based on the location of the eye. Since eye localization typically lacks additional data (such as eye segmentation, corners, etc.) in existing software solutions, and common iris tracking solutions usually involves two steps:(a) The first step includes a rough detection of the iris location, and (b) the second step includes performing an exact localization of the iris. This topic is widely covered in the literature, with many proposed solutions, (e.g.—Deng, Jyh-Yuan, and Feipei Lai. "Region-based template deformation and masking for eye-feature extraction and description." Pattern recognition 30.3 (1997): 403-419). Some of the works are based on edge detection (see Canny, John. "A computational approach to edge detection." Pattern Analysis and Machine Intelligence, IEEE Transactions on 6 (1986): 679-698.), some are model/template based, and some are Hough-transform based (such as Ballard, Dana H. "Generalizing the Hough transform to detect arbitrary shapes." Pattern recognition 13.2 (1981): 111-122).

Different prior art references propose different models of iris tracking—the simplest model composed of the iris center only (without the radius), the most complex model treats the iris as a general ellipse, and in many other works the iris is modeled as a circle. Most of the works do not assume special equipment and allow a generic camera.

The pupil tracking problem deals with extraction of the pupil radius and its location. Typically, the problem is solved based on the location and the radius of the iris (in such case, only the radius of the pupil remains to be detected). The pupil detection problem is a much harder problem than the iris detection one. This is mainly due to contrast resolution issues at the pupil-iris boundary. However, pupil tracking techniques have better accuracy since coverage by eyelids is a lesser concern (except during blinking). Prior art documents that propose a solution to this problem are based on an existing IR illumination in order to enhance the contrast between the pupil and the iris. For example—Mulligan, Jeffrey B. "Image processing for improved eye-tracking accuracy." Behavior Research Methods, Instruments, & Computers 29.1 (1997): 54-65.

Using the very common IR-based methods, the pupil is detected without necessity in iris detection.

Moreover, no prior art document relates to a method to track the pupil using a visible-light camera shooting a non-static head.

Although some prior art references seemingly address pupil tracking, they do not extract the pupil radius, and the solved problem is actually the iris tracking while the iris center is imposed on the pupil center.

It is therefore an object of the invention to provide a method and system for extracting eye markers and deriving capabilities of monitoring and improving cognitive states.

It is another object of the invention to provide a method for tracking the pupil using a visible-light image acquisition device shooting a non-static head.

It is still another object of the invention to extract eye markers from a video stream or file and to detect the pupil.

It is yet another object of the invention to improve eye detection results.

Further purposes and advantages of this invention will appear as the description proceeds.

SUMMARY OF THE INVENTION

In one aspect the present invention relates to a method for monitoring, testing, and/or improving cognitive abilities of a subject, comprising the steps of:
  recording a video of the face and eyes of a subject with an image acquisition device;
  detecting the eye's pupil;
  extracting eye markers from the pupil detected in said video; and
  analyzing said extracted eye markers and deriving insights regarding trends in said subject's cognitive state;
wherein said steps of detecting the pupil and extracting eye markers from said video comprise the steps of:
  detecting the eye and the eye region of the image;
  detecting the iris by receiving as an input said eye region of said detected image, and providing as an output the iris center and radius; and
  detecting and localizing the pupil by receiving as an input said detected iris center and radius and returning the radius of the pupil as output.

In an embodiment of the invention, the method further comprises the use of biofeedback, which comprises the steps of:
  interacting with a subject through a computerized application;
  receiving a derived insights regarding said subject's cognitive state trends and producing an adapted content for said subject, which improves said subject's cognitive abilities in "closed loop", in accordance with the derived insights about said subject's cognitive state.

In an embodiment of the invention, the biofeedback is one of the following:
  a. an engaging task;
  b. a change in subject experience;
  c. a reduction in game score;
  d. a slowing down of the game; and
  e. providing personalized calming content.

In an embodiment of the invention, the image acquisition device is a visible light camera.

In an embodiment of the invention, the step of detecting the pupil and extracting eye markers is done simultaneously for both eyes.

In an embodiment of the invention, in the eye detecting step, a particle filter is used with the best two particles selected in each iteration, and an eye patch is learnt progressively over multiple frames.

In an embodiment of the invention, the iris detecting step comprises the steps of:
  detecting local gradients;
  defining a score to detect a circle located at $(x_0, y_0)$ with a radius $r_0$ according to $$\text{Score} = \int_{\alpha \in [0, 2\pi]} G(x_0 + r_0 \cos\alpha, y_0 + r_0 \sin\alpha) * \begin{pmatrix} \cos\alpha \\ \sin\alpha \end{pmatrix} d\alpha$$

Where $G(x, y)$ is the image gradient at point $(x, y)$, and $$\begin{pmatrix} \cos\alpha \\ \sin\alpha \end{pmatrix}$$

is the gradient at angle $\alpha$ of said circle;
  defining $(x_0, y_0, r_0)$ which give the highest score as the detected iris location and radius; and
  verifying the detected $(x_0, y_0, r_0)$ against a threshold to determine whether a true iris was detected.

In an embodiment of the invention, if the face is detected but the iris is not, a blink detection is assumed.

In an embodiment of the invention, the step of detecting and localizing the pupil comprises the steps of:
  detecting the parts of the iris and its area content, which are occluded by the skin, by checking the angles which do not have strong gradients;
  converting the iris image to gray-level;
  detecting and masking-out the highlights from the surrounding illumination;
  computing a $10^{th}$ percentile intensity value of each radius and providing a function $f(r)$ which is the $10^{th}$ percentile intensity value for each radius r;
  distinguishing between the lower and the higher parts of said function $f(r)$ by selecting a value of which results in the lowest sum of variances of each of the two parts according to:

$$r_0 = \operatorname*{argmin}_{r} \left[ \operatorname*{Var}_{r' < r}(f(r')) + \operatorname*{Var}_{r' > r}(f(r')) \right];$$

and
  returning $r_0$ as the result pupil radius.

All the above and other characteristics and advantages of the invention will be further understood through the following illustrative and non-limitative description of embodiments thereof, with reference to the appended drawings.

DETAILED DESCRIPTION OF EMBODIMENTS OF THE PRESENT INVENTION

The present invention relates to a system and method for pupil tracking and eye-markers extracting using an image acquisition device such as a visible-light camera shooting a non-static head. In an embodiment of the present invention eye-markers are extracted from one eye or from both eyes. The extraction from both eyes uses for averaging the results of the two eyes when abnormalities are detected in one of the eyes.

Figure 11:
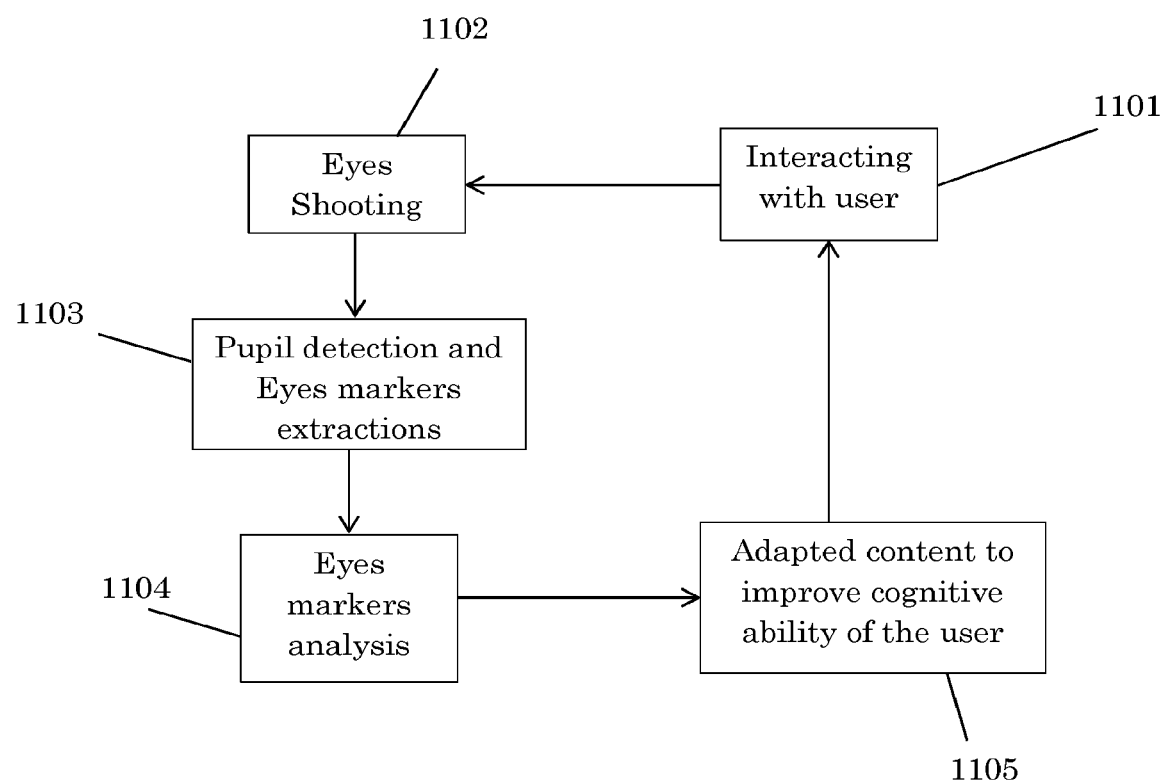
FIG. 11 schematically shows a flow chart of a method according to an embodiments of the present invention.

In addition, and as can be seen in FIG. 11, the invention relates to a computerized application (in a smartphone or a PC) which interacts with a user in step 1101 (for example trough a game or movie, usually in a context of biofeedback), and takes video shooting of the users face and eyes during said interaction, in step 1102. The method of the invention tracks pupil and extracts eye markers using a visible-light camera shooting a non-static head. According to the present invention the eye markers are extracted in step 1103, such as data about the extraction and contraction of the pupil, the distance between the pupils, and eye movement. After extracting the eye markers, said extracted eye markers are analyzed in step 1104 and insights are derived regarding the cognitive state of the user. As a result, if necessary, in step 1105, an adapted content is produced for the user, which improves said user cognitive ability in accordance with the derived insights about his cognitive state.

In one embodiment the eye markers are extracted from a video stream or file.

In another embodiment, the eye markers are extracted in real-time, directly from the camera.

Figure 12:
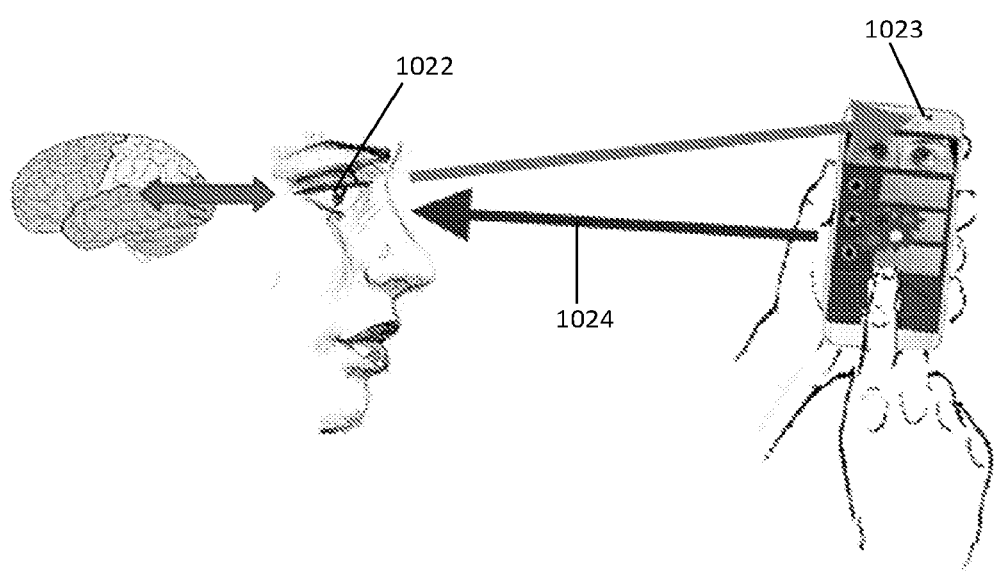
FIG. 12 schematically shows a diagram describing the biofeedback of the invention.

In an embodiment of the invention, a biofeedback is used in the invention. FIG. 12 schematically shows a diagram describing the biofeedback of the invention. A Bio-eye sensor 1023, enables the system of the invention to utilize eye-biomarkers extracted from the pupil 1022 (including but not limited to pupil dilation, eye-movements, and blinks) to monitor the user's cognitive state (including the level of attention, cognitive load and emotional state). Then, if desired, it is possible to present the user with content-feedback 1024 supporting a desired change in this cognitive state. There are several methods of analysis to extract eye-biomarkers from the eye and pupil signal, used in the present invention. For example: (a) taking advantage of the pupil's dilatory response to cognition-stimulating events. (b) analyzing the frequency-dynamics of pupil fluctuations in order to determine the state of mental effort and emotion; and (c) studying eye movements and defines their normal properties vs abnormalities suggesting possible psychiatric pathology Examples for Improving Cognitive State Using Biofeedback:

Improve attention: it is possible to immerse the user in an engaging task (e.g., movie or game) and change user experience whenever loss of attention is detected (e.g. make movie darker or slower; alternatively, in context of game-based biofeedback, it is possible to make change dynamics according to the present invention: reducing score, slowing game etc.).

Improve learning effectiveness: learning material may be tuned, to maintain an optimal cognitive load (i.e. just at the right level, not too easy and not too hard, so it is neither boring nor overwhelming for users).

Improve emotional state: stress or emotional distress may be overcome by providing personalized calming content (visual and/or auditory) until eye markers indicate relaxation has been achieved.

Figure 1:
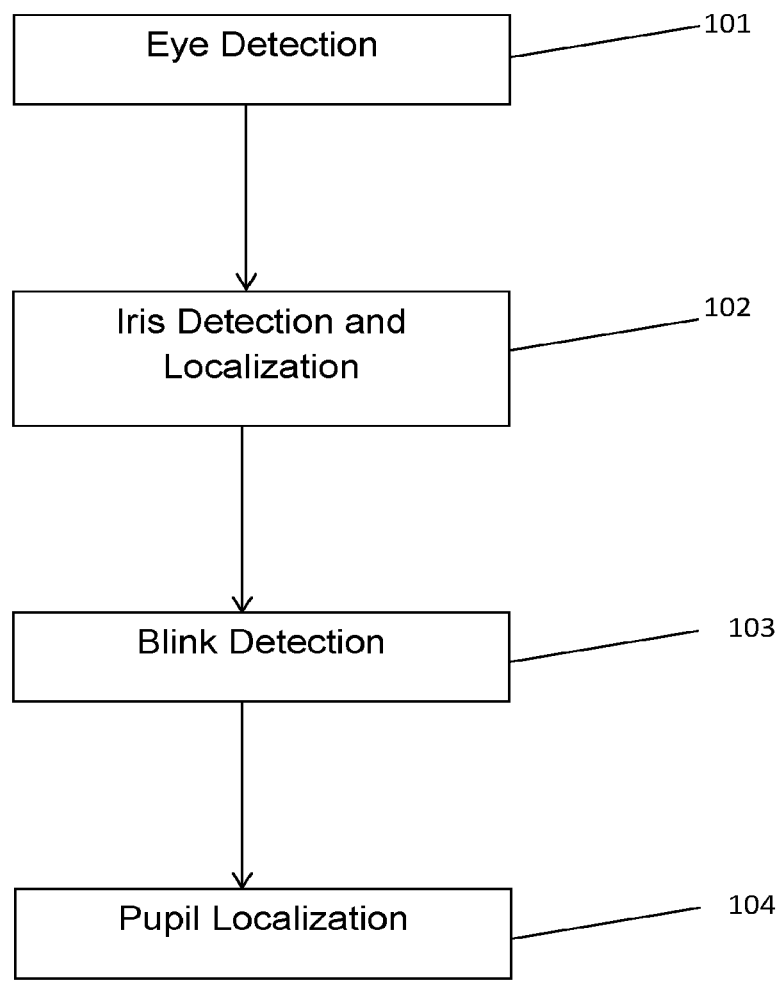
FIG. 1 schematically describes the method of pupil detection according to an embodiment of the present invention.

FIG. 1. Schematically describes the main steps of the method of pupil detection of the present invention. The method of pupil detection of the present invention is divided into four steps: the first step 101 is the Eye detection, the second step 102 is the Iris detection and localization, the third step 103 is the Blink detection and the fourth step 104 is the Pupil localization.

The eye detection step 101, is done to determine the rough location of the eye, in order to perform the later steps (iris and pupil localization) in a limited region.

The eye detection step 101 is based on a face detection module well known in the art (for example: OpenCV).

First, the image (specifically, its middle part) brightness and contrast are adjusted, and the histogram is equalized. This prepares the image for the face detection.

Following, the face detection routine of the face detection module is called. If more than one face is detected, the detection is halted. In the next step, the eyes are detected using the face detection module's eye detection cascade. The detection is independent of the face detection. Finally, the eye locations (there can be many "eyes" in the image) are verified based on the face location and size. Detected eyes which are not in the upper half of the detected face are discarded.

However, the eye detection of the face detection module, returns many false-positives of the eye locations. Therefore the present invention improves on the existing solution with the following two post-processing methods which are used to deal with this problem:

1. A particle filter is used with the best two particles selected in each iteration. A "particle filter" is a well know statistical method for removing noise from a signal (Del Moral, Pierre (1996). "Non Linear Filtering: Interacting Particle Solution." (PDF). Markov Processes and Related Fields 2 (4): 555-580).

In the case of the present invention pruning of subtle pixel-level noise in the sub-image which covers the eye (i.e. "eye patch").

Particles are defined as: the detected eye locations (in many frames, more than 2) and the weights are the distance to the locations in the current frame. Using the filter, the returned eye location moves far away from the previous location only if the new location has a support over several frames. Furthermore, random false-positives are neglected.

2. Eye patch (the sub-image which covers the eye) is "learnt" (accumulated) over several dozens of frames. In this way, in every frame the eye appearance over the last several seconds is available. The exact location of the eye is found using maximal cross-correlation with the known eye appearance. The output of the eye detector filtered by the particle filter is used only as a regularizer to the eye patch location.

As a result of these two post-processing steps, the output of the eye detection module of the present invention becomes more robust (no more "jumps" and exactly two eye locations are returned), more trustable (it is found based on the true eye appearance and not on a machine-learning-based detected), and faster.

Figure 2:
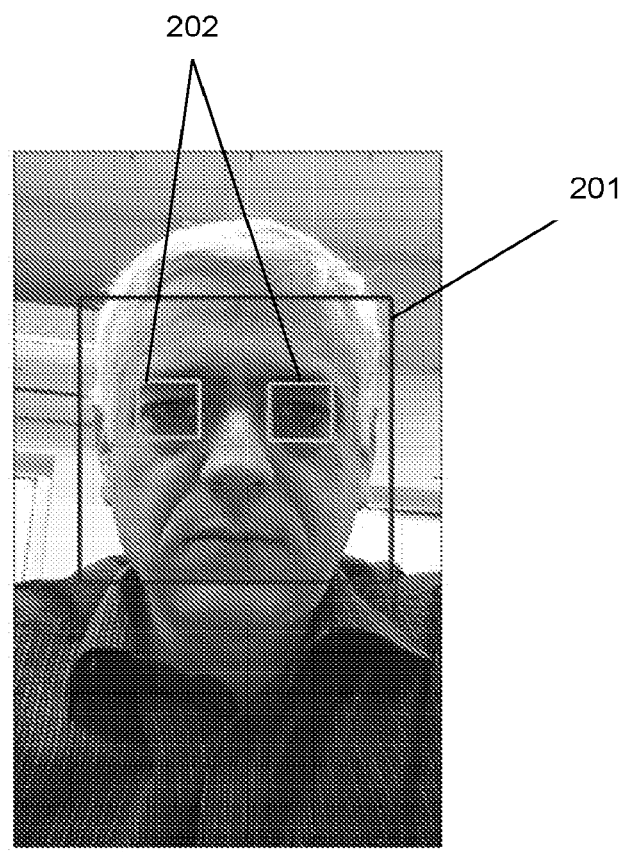
FIG. 2 schematically shows an example of the result of the face detection and eye detection in an image.

FIG. 2 presents a sample result of the eye detection process. First the face of the man 201 is detected and then the eyes 202 are detected.

After the eye detection step 101, the iris detection is a necessary step for the pupil detection. The iris is much more prominent in the image than the pupil, thus it is much easier to detect. In addition, it can be practically assumed that the pupil center is the same as the iris center. Thus, in order to localize the pupil center, it is needed to solve the iris detection problem.

Figure 3:
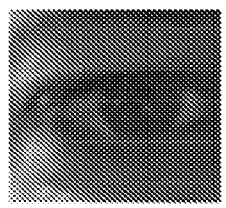
FIG. 3 schematically shows an example of the eye region used for iris detection.

The input to this step 102 of iris detection is the eye region of the image, detected in the previous step of eye detection 101, as shown for example in FIG. 3 in continuation to the example of FIG. 2.

The purpose of this step 102 is to detect a circular object with an edge separating between brighter and darker parts of the image. In other words, it is first needed to detect the image gradients which are a directional changes in the intensity or color in an image.

Figure 4:
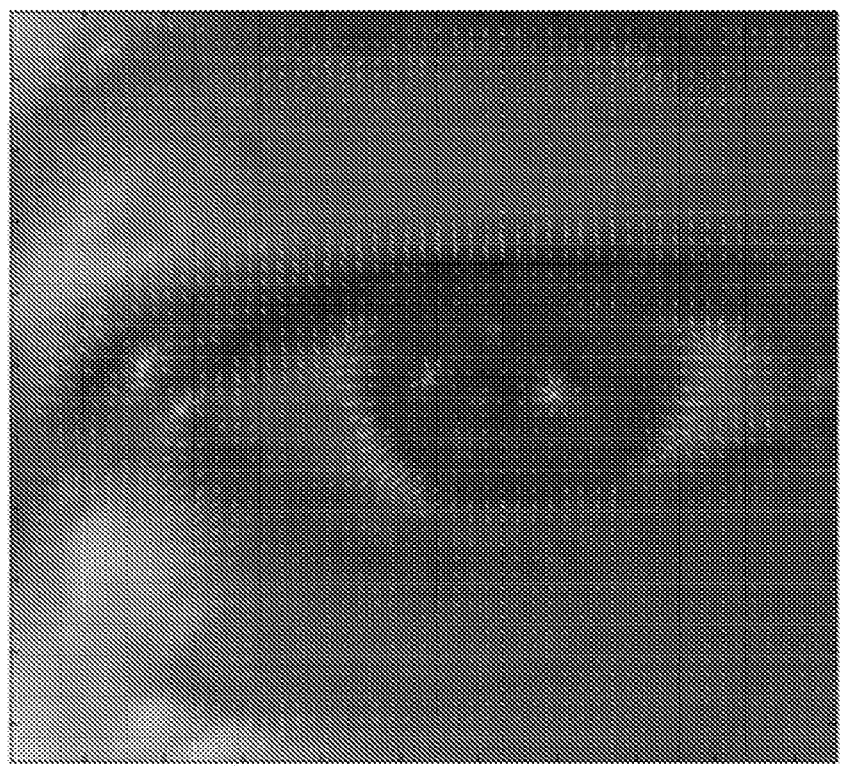
FIG. 4 schematically shows an example of the local gradient found in the eye region.

The gradients are found in the image, based on all three (RGB) channels, as can be seen in FIG. 4, where local gradient are marked in a picture of an eye.

Next, a score is defined for a circle located at $(x_0, y_0)$ with a radius $r_0$:

$$\text{Score} = \int_{\alpha \in [0, 2\pi]} G(x_0 + r_0\cos\alpha, y_0 + r_0\sin\alpha) * \begin{pmatrix} \cos\alpha \\ \sin\alpha \end{pmatrix} d\alpha$$

Where G(x, y) is the image gradient at point (x, y), and $$\begin{pmatrix} \cos\alpha \\ \sin\alpha \end{pmatrix}$$

is the gradient at angle α of the theoretical circle for which the score is computed.

The parameters $(x_0, y_0, r_0)$ which give the highest score are the detected iris location and radius.

A threshold is defined as:

threshold=minScore*strengthFactor where minScore is a constant with value of 223; and strenthFactor is 1.0 if previous iris info still valid, and 1.25 if not.

The score is verified against said threshold to determine whether a true iris was detected or some random location in an image which does not contain an iris at all. The latter case (i.e. a false detection of an iris) can happen due to two possible reasons:

1. The eye is closed.
2. The Eye Detection step returned a false positive.

The threshold is derived from the gradient statistics in the image.

Figure 5:
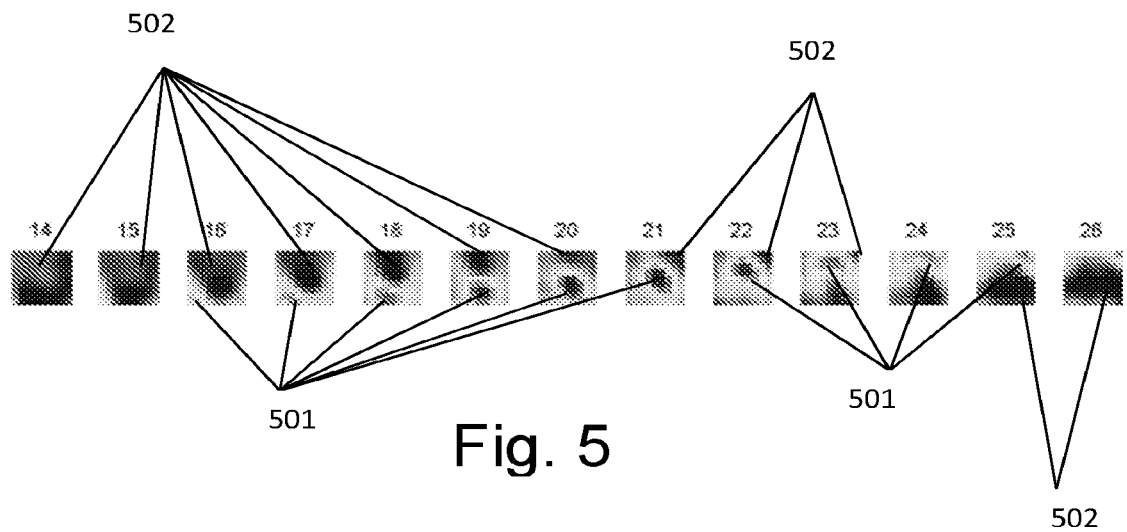
FIG. 5 schematically shows an example of the response for a certain radius for all the tested iris locations.

In order to verify that the method described above is generally correct, i.e., the detected iris parameters are the true iris location and not due to a random peak in the response function, the present invention visualizes the response function in all three dimensions in the vicinity of the detected parameters. FIG. 5 shows the responses in the x-y plane for each radius.

Each image in FIG. 5 represents the response for a certain radius for all the tested iris center locations. 501 are strong response and 502 are weak response. The strong peak in the image corresponding to 20 pixel radius suggests that the response is real and not random.

Figure 6:
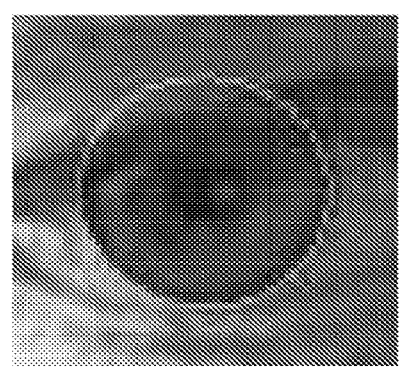
FIG. 6 schematically shows the iris parameters that correspond to the peak in the response function.
Figure 7:
FIG. 7 schematically shows an example of a detected iris.

FIG. 6 shows the iris parameters that correspond to the peak in the response function. FIG. 7 schematically shows an example of a detected iris.

The verification above was done for many cases, and for all of them the response seemed prominent. However, when the search space is expanded, there are cases where there is another local optimum away from the true iris location, which is better than the response in the true iris location. Such false positives can be detected using method for eye center localizations by means of gradients, and by modifications to the score calculation (e.g. to limit the weight of strong gradients in order to reduce the ability of strong edges in the image to pull away from the right solution).

In an embodiment of the invention, when the exact eye location is known, the iris location changes relatively to the eye location only due to eye movements and then the face movement can be cancelled out.

Due to this improvement, and as the iris movement is small (relative to the eye location), it can be assumed that the iris location did not change much from the previous frame. This fact is used to greatly speed-up the processing and to make the iris detection more robust. In this case the run-time performance is greatly improved. Assuming a video has "normal" eyes (the eyes are not closed for more than 0.5 seconds, the viewer is looking at the camera, etc.), the frames are processed about 6-8 times faster than in the case where iris location changes from frame to frame.

However, if during several frames it is not detected that the iris near the previously known iris location, a full search in the eye region is performed.

In an embodiment of the invention blinks are detected. A non-detected iris is a strong indicator of a blink (the iris is not visible), and the present invention treats a non-detected iris (assuming the face is detected) as a blink detection. In one embodiment of the method of the present invention, the blink detection algorithm relies completely on the quality of the iris detection. However, in another embodiment of the invention a separate blink detection algorithm is based on skin detection, machine learning, verification against neighboring frames or other methods.

The last step of the method of pupil detection in the present invention is the pupil localization step 104 (FIG. 1). The pupil is a darker circle located inside a larger circle (the iris), which has a relatively constant color. The circles have a common center. In order to distinguish between the pupil and the iris, and find the pupil radius, the pixels of the pupil and the iris should contain statistically (considering the noise) different values. The possibility to detect the pupil radius strongly depends on the specific video—its resolution, noise, illumination, and on the iris color of the analyzed eye. Bright iris colors are easier than dark ones.

The input to this step 104 of pupil localization, are the iris parameters (center and radius), whose detection is described in the step 102 of iris detection.

The purpose of step 104 is to find the radius of the pupil, as its center is identical to the center of the iris.

Figure 8:
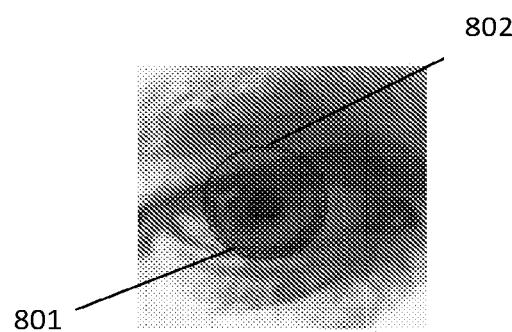
FIG. 8 schematically shows an example of the parts of the iris which are occluded by the skin and are detected.

First, the parts of the iris that are occluded by the skin are detected, by checking the angles that do not have strong gradients; i.e. assuming color and intensity representation of the eyelid in an image is significantly different than that of the iris, the algorithm finds angles along which moderate change in color and intensity convey position of eyelid relative to the iris. These heuristics are demonstrated by the two circles 801 and 802 in FIG. 8. Part of the iris is visible 801, and part is hidden under the eyelid 802.

Then, the following steps are performed:
1. Convert the iris to gray-level.
2. Detect and mask-out the highlights from the surrounding illumination.
3. Compute the $10^{th}$ percentile intensity value of each radius. Generally speaking, using the 10th percentile implies using the top 10% according to a sort based on some measure (in this case, the radius of the pupil). According to the present invention a 1 dimensional vector of intensities is formed, starting from the center of the pupil (which is darkest) and moving out to towards the iris (which is expected to be a bit brighter at least at outskirts). The border of the pupil radius is defined using the start point of the 10th percentile in grey-level intensity.

Figure 9:
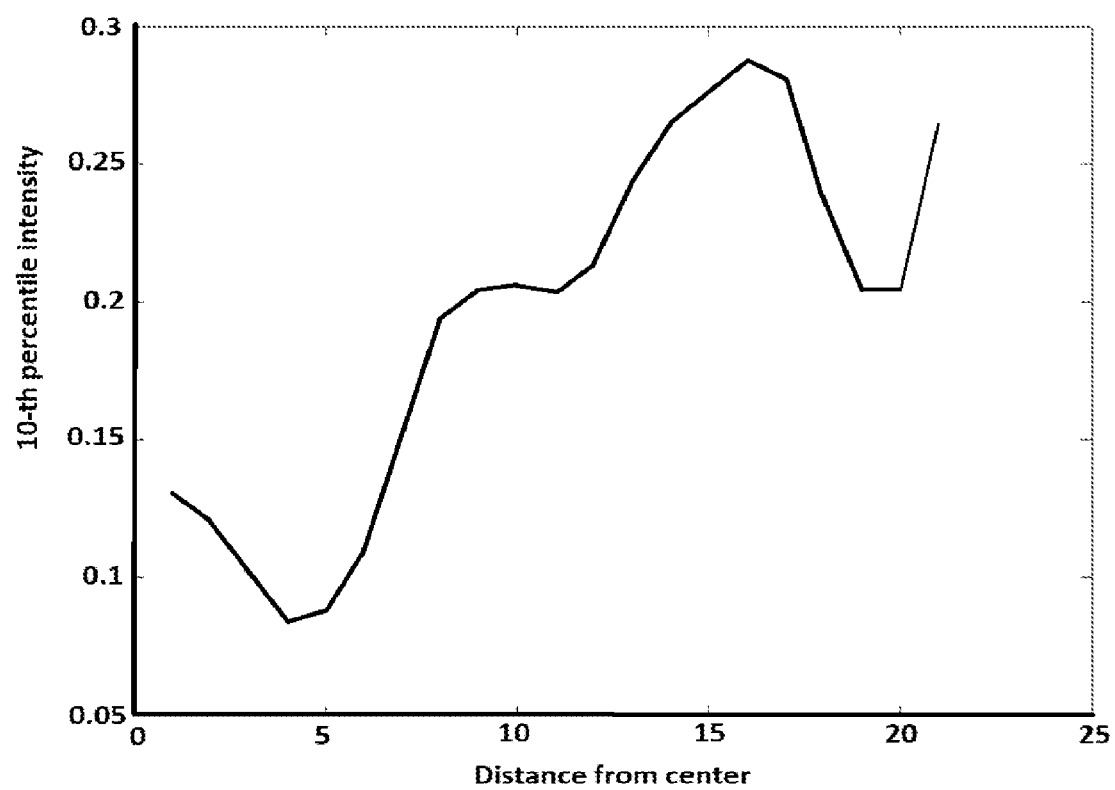
FIG. 9 schematically shows an example of a graph of the $10^{th}$ percentile intensity as a function of the distance from the center of the pupil/iris.

The result is a 1D function, f(r), where r is the radius and f(r) is the $10^{th}$ percentile intensity. The function should return lower intensities for small values of r (the pupil) and higher intensities for large values of r (the iris). FIG. 9 schematically shows an example of a graph of the $10^{th}$ percentile intensity as a function of the distance from the center of the pupil/iris (i.e. the radius).

Figure 10:
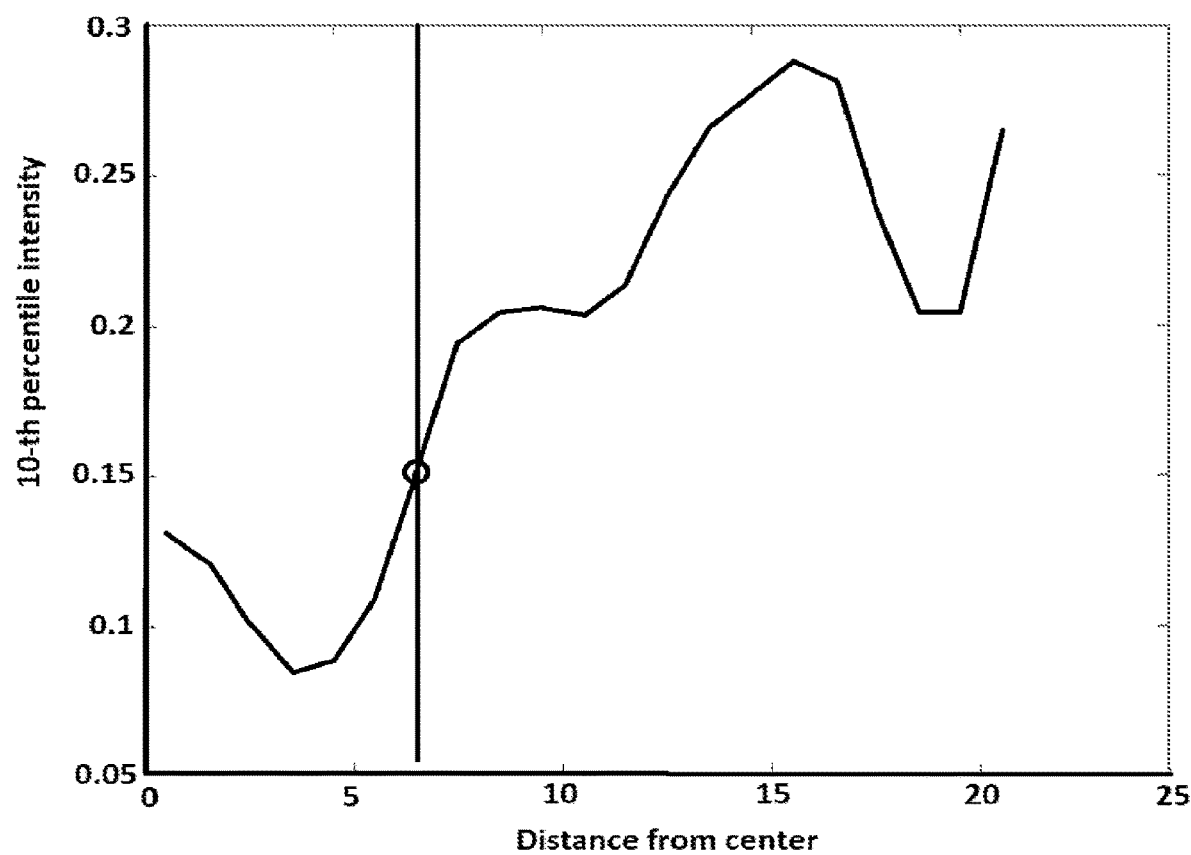
FIG. 10 schematically shows an example of the returned pupil radius.

As a final step, the method of the present invention distinguishes between the lower and the higher parts of the function by selecting a value $r_0$ of which results in the lowest sum of variances of each of the two parts, and as can be seen in FIG. 10.

The $r_0$ is calculated according to:

$$r_0 = \underset{r}{\operatorname{argmin}}\left[\underset{r'<r}{\operatorname{Var}(f(r'))} + \underset{r'>r}{\operatorname{Var}(f(r'))}\right]$$

$r_0$ is the returned pupil radius.

In an embodiment of the invention, instead of collapsing the pupil information to 1D function, all pupil pixels are analyzed.

At first, a mask that removes the high-lighted and skin pixels is applied. Following, the pupil radius is computed. This is the radius r that minimizes the following:

$$\lambda \sum_{x\in Pupil(r)}(x-\bar{x})^2 + (1-\lambda)\sum_{y\notin Pupil(r)}(y-\bar{y})^2$$

where $\lambda$ is a weighting factor, which is set to 0.7, and x and y are pixel intensity values.

The confidence score of the pupil with a given radius r is:

$$s = \frac{|\bar{x}-\bar{y}|}{\sqrt{\operatorname{var}(x)+\operatorname{var}(y)}}$$

Which is normalized to a [0,1] range, so that s=1 becomes 0.1 and s=2 becomes 0.9 (these values were empirically found as "bad" and "good" confidence):

$$s' = \frac{1}{1+e^{(-s+1.5)-4.395}}$$

The confidence score is the system output, and it is used in the averaging post-processing step of the pupil values of the two eyes (pupil with higher confidence has a higher weight in the averaging).

The usual recording distance from the phone camera is about 30 cm. The diameter of the human iris, is about 11-12 mm.

Generally, for cameras with a standard field of view, such as SGS3 or iPhone 4:

$$\text{pixel\_per\_mm} \cong 100 \cdot \frac{\sqrt{\text{image\_resolution\_in\_MP}}}{\text{plane\_distance\_in\_cm}}$$

Thus, the diameter of the iris in an image is about 40 pixels according to the following calculation:

$$\frac{100\sqrt{1.280 \cdot 0.720}}{30} \cdot 12 \cong 40.$$

In an embodiment of the invention, the motion blur problem is addressed by taking advantage of multiple frames from the video rather than working frame by frame. As data is repeated and the underlying data in high frequency sampling is constant, while the motion blur is an additive noise, it can significantly improve/remove it.

Another problem with which the present invention deals is the glasses problem. Glasses may affect the detection for several reasons:
1. The detected object (eyes, iris or pupil) may be occluded by the glasses frame.
2. The glasses lens may introduce geometric distortion, lower contrast or color tint.
3. Stains on the glasses may interfere with the image of the detected object.

In an embodiment of the invention, in case where the user has glasses or eye contact an auto compensate for glasses and contact lenses identification is operated, and a geometric correction (as if using a complementary lens) may be applied. In another embodiment of the invention, the method of the invention manages with reduced field of view (when eyes are partially shut) to an extent, as interference with view are expected to be minimal, as significant interference will disturb the user.

In an embodiment of the invention, optimal quality stills photos are taken in parallel to video, with max resolution, smallest aperture (if/when dynamic), optimal ISO (probably lowest possible, higher if it is must for poor lighting conditions), optimized shutter speed (slowest possible depending on stability indications by accelerometer, trial and error, etc.), spot metering mode (to pupil), optimized white-balancing, optimize/enhance dynamic range. The present invention uses stills photos to improve/correct accuracy and to compensate lighting configuration to determine actual lighting condition.

In an embodiment of the invention, lighting conditions/changes are measured/tracked through pixel brightness in different eye sections and compensate for changes. Alternatively, average brightness of all pixels in images recorded by the front\back camera may indicate such changes in lighting conditions.

In an embodiment of the invention, the distance is normalized by measuring change in face size (use constant features regardless of expressions). A standard feature/measure is the distance between the eyes, However, the present invention can use other features such as face width at eyes, etc.

In an embodiment of the invention, head/face orientation is normalized, including compensation for elliptical iris/pupil.

Due to the nature of the eye, many parameters change only a little between adjacent frames and this fact can be used for a more stable solution:

For the eye detection stage: the eye shape and its rough location.

For the iris detection stage: radius, rough location, and color.

For the pupil radius detection stage: The pupil radius.

In an embodiment of the invention, the iris detection algorithm can be improved by using information other than the iris circle: the eye shape, the eye color. Furthermore, model-based methods, such as RANSAC and Hough transform (which are common feature extraction techniques used in image analysis to identify imperfect instances of geometric shapes (in our case a circle or ellipse)), have to be considered.

In an embodiment of the invention, other problems the invention deals with are:

Accuracy: A dynamic model (e.g., particle filter) and super-resolution techniques can be used through multiple consecutive frames to obtain sub-pixel accuracy. Also, occasional high quality still pictures can be taken to further improve and tune the accuracy.

Dynamic lighting: the (front) camera brightness can be controlled/optimized to improve the dynamic range of extracted objects (specifically, eyes and pupil).

Dark eyes: the 'red' colors of the spectrum can be filtered, and this mode can be used as an approximation of the IR camera (including IR spectrum if/when not filtered by the camera).

Dynamic background: using eye detection methods described above, all redundant background can be filtered out.

Personalized calibration: in the embodiment of the present invention, the system is calibrated for current user and settings, and is switched to tracking mode (see below). In case of tracking loss, the system performs a fresh acquisition (and re-calibration), and when ready, it switches back to tracking mode.

Latency & Real-time: algorithms and performance are optimized to provide fastest (minimal latency—milliseconds) extraction and delivery of the extracted measures. In cases of heavy processing (e.g., re-calibration) or insufficient processing resources, a reduced frame rate may be used to maintain real-time delivery.

Although embodiments of the invention have been described by way of illustration, it will be understood that the invention may be carried out with many variations, modifications, and adaptations, without exceeding the scope of the claims.

The invention claimed is:

1. A method for monitoring, testing, and/or improving cognitive abilities of a subject, comprising the steps of:
    a. recording a video of the face and eyes of a subject with an image acquisition device;
    b. detecting a pupil using image processing algorithms;
    c. extracting eye markers from the pupil detected in said video; and
    d. analyzing said extracted eye markers and deriving insights regarding trends in said subject's cognitive state;
    wherein said steps of detecting the pupil and extracting eye markers from said video comprise the steps of:
    I. detecting a face, followed by an eye and an eye region of the image;
    II. detecting an iris by receiving as an input said eye region of said detected image, and providing as an output an iris center and radius; and
    III. detecting and localizing the pupil by receiving as an input said detected iris center and radius and returning a radius of the pupil as output.

2. A method according to claim 1, wherein the image acquisition device is a visible light camera.

3. A method according to claim 1, wherein the step of detecting the pupil and extracting eye markers is done simultaneously for both eyes.

4. A method according to claim 1, wherein, in the eye detecting step, a particle filter is used with the best two particles selected in each iteration, and an eye patch is learnt progressively over multiple frames.

5. A method according to claim 1, wherein if the face is detected but the iris is not, a blink detection is assumed.

6. A method according to claim 1, wherein the recording step comprises recording in the visible light or in the near IR spectrum.

7. A method according to claim 1, wherein, during the recording step, a head of the subject is non-static.

8. A method according to claim 1, further comprising performing the steps of detecting the pupil and extracting eye markers through analysis of multiple frames of the video simultaneously, to thereby identify noise generated by motion blur.

9. A method according to claim 1, further comprising capturing one or more still photographs simultaneously with the recording of the video, and using said still photographs to compensate for lighting conditions in the video.

10. A method according to claim 1, wherein the extracted eye markers comprise pupil diameter, pupil center location, distance between the pupils, eye movements, blinks, and changes in each of the foregoing markers over time.

11. A method according to claim 10, wherein the step of extracting eye markers comprises showing cognition stimulating events to the subject, and monitoring the pupil's dilatory response to said cognition-stimulating events.

12. A method according to claim 10, wherein the step of extracting eye markers comprises analyzing relative frequency dynamics of pupil fluctuations in both eyes, and further comprising determining a state of mental effort and emotion on a basis of said frequency dynamics.

13. A method according to claim 10, wherein the step of extracting eye markers comprises defining normal properties of eye movements for the subject.

14. A method of according to claim 1, further comprising performing blink detection with a machine learning algorithm incorporating analysis of eye aspect ratio.

* * * * *